United States Patent
Miyake et al.

(10) Patent No.: US 12,116,328 B2
(45) Date of Patent: Oct. 15, 2024

(54) 11-HALO-3-UNDECENE COMPOUND AND A PROCESS FOR PREPARING THE SAME AND A PROCESS FOR PREPARING 9-DODECENAL COMPOUND

(71) Applicant: Shin-Etsu Chemical Co., Ltd., Tokyo (JP)

(72) Inventors: Yuki Miyake, Niigata (JP); Takeshi Kinsho, Niigata (JP); Ryo Komatsu, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/922,679

(22) Filed: Jul. 7, 2020

(65) Prior Publication Data
US 2021/0009489 A1  Jan. 14, 2021

(30) Foreign Application Priority Data
Jul. 9, 2019  (JP) .................. 2019-127829

(51) Int. Cl.
| C07C 17/263 | (2006.01) |
| A01N 29/02 | (2006.01) |
| C07C 17/275 | (2006.01) |
| C07C 41/50 | (2006.01) |
| C07C 45/42 | (2006.01) |

(Continued)

(52) U.S. Cl.
CPC .......... *C07C 17/2632* (2013.01); *A01N 29/02* (2013.01); *C07C 17/275* (2013.01); *C07C 41/50* (2013.01); *C07C 45/42* (2013.01); *C07C 21/02* (2013.01); *C07C 21/04* (2013.01)

(58) Field of Classification Search
None
See application file for complete search history.

(56) References Cited

U.S. PATENT DOCUMENTS

2014/0275656 A1* 9/2014 Miyake .................. C07C 21/215
570/189
2018/0305284 A1* 10/2018 Miyake .................. C07C 21/04
2021/0130270 A1* 5/2021 Wampler ................ C07C 17/16

FOREIGN PATENT DOCUMENTS

| CN | 106632162 A * 5/2017 |
| EP | 0038052 A1   10/1981 |
| JP | S58177924 A  10/1983 |

OTHER PUBLICATIONS

Crombie, L. "Amides of vegetable origin. II. Stereoisomeric N-isobutyl-1,5-nonadiene-1-carboxamides and the structure of pellitorine" Journal of the Chemical Society, 4338-46; 1952 (Year: 1952).*

Sasaerila, Y. et al. "Sex pheromone components of nettle caterpillar, *Setora nitens*" Journal of Chemical Ecology, vol. 26, No. 8, 2000, 1983-1990 (Year: 2000).*

Vendors (pp. 1-56) (Year: 2021).*

Accela ("1-bromo-5-chloropentane" deposited and available Feb. 22, 2019) (Year: 2019).*

Johnson (Johnson, D K et al. "Dilithium Tetrachlorocuprate Catalyzed Coupling of Allylmagnesium Bromide With α,ω-Dihaloalkanes" Synthetic Communications, 24(11), 1557-1564 (1994)) (Year: 1994).*

(Continued)

*Primary Examiner* — Medhanit W Bahta
(74) *Attorney, Agent, or Firm* — Myers Bigel, P.A.

(57) ABSTRACT

The present invention provides a process for preparing an 11-halo-3-undecene compound (7) in which $X^1$ represents a halogen atom, the process comprising a step of subjecting a nucleophilic reagent, 3-hexenyl compound (5): in which $M^2$ represents Li or $MgZ^2$, wherein $Z^2$ represents a halogen atom or a 3-hexenyl group, to a coupling reaction with a 1-halo-5-halopentane compound (6) in which $X^3$ and $X^4$ may be same with or different from each other and represent a halogen atom, to produce the 11-halo-3-undecene compound (7). The present invention also provides a process for preparing a 9-dodecenal compound (4): the process comprising a step of subjecting a nucleophilic reagent, 8-undecenyl compound (1) in which $M^1$ represents Li or $MgZ^1$, wherein $Z^1$ represents a halogen atom or an 8-undecenyl group, and an orthoformic ester compound (2) in which R may be same with or different from each other and represents an alkyl group having 1 to 6 carbon atoms, to a nucleophilic substitution reaction to produce a 1,1-dialkoxy-9-dodecene compound (3) in which R are as defined above; and hydrolyzing the 1,1-dialkoxy-9-dodecene compound (3) thus obtained to produce the 9-dodecenal compound (4).

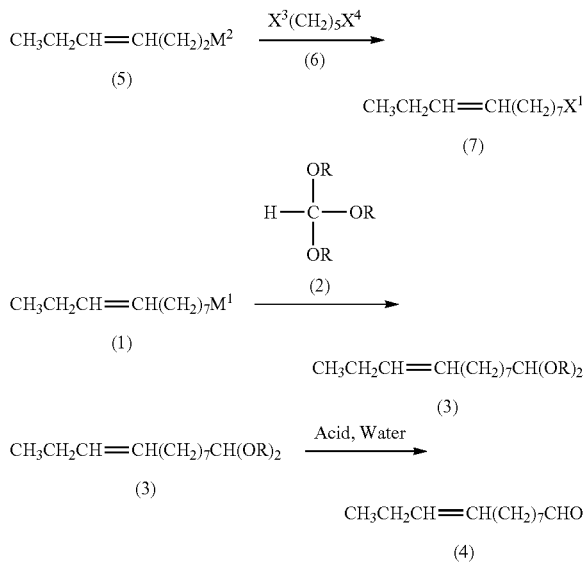

4 Claims, No Drawings

(51) Int. Cl.
C07C 21/02 (2006.01)
C07C 21/04 (2006.01)

(56) References Cited

OTHER PUBLICATIONS

Akos "(Z)-1-chlorohex-3-ene" deposited and available on Jan. 24, 2012 (Year: 2012).*
Patent No. CN106632162A, machine translation, May 10, 2017; pp. 1-8 (Year: 2017).*
Akos II "(E)-1-chlorohex-3-ene" deposited and available on Sep. 22, 2016 (Year: 2016).*
Sasaerila et al. "Identification of Sex Pheromone Components of Nettle Catepillar, *Setothosea asigna*" Journal of Chemical Ecology, 23(9):2187-2196 (1997).
Sasaerila et al. "Decadienoates: Sex Pheromone Components of Nettle Caterpillars *Darna trima* and *D. bradleyi*" Journal of Chemical Ecology, 26(8):1969-1981 (2000).
Tidwell, Thomas T. "Oxidation of Alcohols to Carbonyl Compounds via Alkoxysulfonium Ylides: The Moffatt, Swern, and Related Oxidations" Organic Reactions, 39:297-572 (1990).
Extended European Search Report corresponding to European Patent Application No. 20184239.0 (7 pages) (dated Dec. 7, 2020).
Jurgen Bestmann et al. "Pheromone, VII. Synthese von 1-substituierten (Z)-9-Alkenen" Chemische Berichte, 108(11):3582-3595 (1975) (English translation of abstract).
Agrawal et al. "Iron-Catalyzed Cross-Coupling Reactions of Alkyl Grignards with Aryl Sulfamates and Tosylates" Organic Letters, 15(1):96-99 (2013).
Dahadha et al. "Carbon-carbon cross-coupling reactions of organomagnesium reagents with a variety of electrophilic substrates mediated by iron catalysts" Organic Communications, 14(1):1-38 (2021).
Terao et al. "Ni- or Cu-Catalyzed Cross-Coupling Reaction of Alkyl Fluorides with Grignard Reagents" Journal of the American Chemical Society, 125(19):5646-5647 (2003).

* cited by examiner

11-HALO-3-UNDECENE COMPOUND AND A PROCESS FOR PREPARING THE SAME AND A PROCESS FOR PREPARING 9-DODECENAL COMPOUND

TECHNICAL FIELD

The present invention relates to an 11-halo-3-undecene compound and a process for preparing the same and a process for preparing a 9-dodecenal compound.

BACKGROUND ART

*Setothosea asigna* and *Setora nitens*, which are a kind of Nettle caterpillar, are serious pests against palms in Southeast Asia. These pests eat palm leaves to kill the trees. This causes a problem that a yield of palm fruits is seriously reduced. Further, these pests injure also young trees, which is a major problem in raising plantations. At present, insecticides are used. Coconut oil is used also as food. Therefore, residual pesticide may be problematic. Accordingly, biological control methods have been attracting attention, and utilization of sex pheromone substances is expected as one of them (Non-Patent Literatures 1 and 2, as listed below).

It is reported that a sex pheromone of *Setothosea asigna* is a mixture of (9E)-9,11-dodecadienal and (9E)-9-dodecenal (Non-Patent Literature 1). Further, it is reported that a sex pheromone of *Setora nitens* is a mixture of (9Z)-9,11-dodecadienal and (9Z)-9-dodecenal (Non-Patent Literature 2).

The following methods are reported to produce these sex pheromones. It is reported that (9E)-9-dodecenal, sex pheromone of *Setothosea asigna*, can be produced by pyridinium chlorochromate (PCC) oxidation of (9E)-9-dodecenol (Non-Patent Literature 1). It is reported that (9Z)-9-dodecenal, sex pheromone of *Setora nitens*, can be produced by pyridinium chlorochromate (PCC) oxidation or Swern oxidation of (9Z)-9-dodecenol (Non-Patent Literatures 2 and 3, as listed below).

LIST OF THE PRIOR ART

Non-Patent Literatures

[Non-Patent Literature 1] Gerhard, Gries et al., 1997, J. Chem. Ecol. 23 (9): 2187-2196.
[Non-Patent Literature 2] Gerhard Gries et al., 2000, J. Chem. Ecol. 26 (8): 1969-1981.
[Non-Patent Literature 3] Tidwell Thomas T., 1990, Organic Reactions, 39, "Oxidation of Alcohols to Carbonyl compounds via Alkoxysulfonium Ylides: The Moffatt, Swam, and Related Oxidations."

SUMMARY OF THE INVENTION

However, the production methods reported in Nat-Patent Literatures 1 and 2 comprise an oxidation reaction with a chromium compound having an extremely large environmental load and, further, the oxidation reaction often involves a danger of explosion. Accordingly, implementation of the methods in an industrial scale is difficult.

In the production method repotted in Non-Patent Literature 3, a toxic carbon monoxide gas and bad-smelling dimethyl sulfide are by-produced, so that a special reaction apparatus is required, and implementation in an industrial scale is difficult. Another problem is that the yield in the reaction is as low as 19%.

The present invention aims it to overcome the aforesaid problems of the prior art, and provides an 11-halo-3-undecene compound which is useful as an intermediate for a nucleophilic reagent used in preparing a 9-dodecenal compound, a method of preparing the 11-halo-3-undecene compound, and a method for preparing a 9-dodecenal compound using the 11-halo-3-undecene compound.

As a result of the intensive researches, the present inventors have prepared an 11-halo-3-undecene compound, and further found that the 9-dodecenal compound can be prepared efficiently and with a high geometric purity using the 11-halo-3-undecene compound, and thus have completed the present invention.

According to one aspect of the present invention, there is provided a process for preparing an 11-halo-3-undecene compound of the following general formula (7):

$$CH_3CH_2CH{=}CH(CH_2)_7X^1 \qquad (7)$$

in which $X^1$ represents a halogen atom,
the process comprising a step of
subjecting a nucleophilic reagent, 3-hexenyl compound, of the following general formula (5):

$$CH_3CH_2CH{=}CH(CH_2)_2M^2 \qquad (5)$$

in which $M^2$ represents Li or $MgZ^2$, wherein $Z^2$ represents a halogen atom or a 3-hexenyl group,
to a coupling reaction with a 1-halo-5-halopentane compound of the general formula (6):

$$X^3(CH_2)_5X^4 \qquad (6)$$

in which $X^3$ and $X^4$ may be same with or different from each other and represent a halogen atom,
to produce the 11-halo-3-undecene compound (7).

According to another aspect of the present invention, there is provided a process for preparing a nucleophilic reagent, 8-undecenyl compound, of the following general formula (1):

$$CH_3CH_2CH{=}CH(CH_2)_7M^1 \qquad (1)$$

in which $M^1$ represents Li or $MgZ^1$, wherein $Z^1$ represents a halogen atom or an 8-undecenyl group,
the process comprising a step of
the aforesaid process for preparing the 11-halo-3-undecene compound (7); and
preparing the nucleophilic reagent, 8-undecenyl compound (1), from the 11-halo-3-undecene compound (7) thus obtained.

According to another aspect of the present invention, there is provided a process for preparing a 9-dodecenal compound of the following formula (4):

$$CH_3CH_2CH{=}CH(CH_2)_7CHO \qquad (4)$$

the process comprising steps of
the aforesaid process for preparing the nucleophilic reagent, 8-undecenyl compound (1);
subjecting the nucleophilic reagent, 8-undecenyl compound (1) thus obtained to a nucleophilic substitution reaction with an orthoformic ester compound of the following general formula (2):

$$\begin{array}{c} \text{OR} \\ | \\ \text{H} - \text{C} - \text{OR} \\ | \\ \text{OR} \end{array} \qquad (2)$$

in which may be same with or different from each other and represents an alkyl group having 1 to 6 carbon atoms,
to produce a 1,1-dialkoxy-9-dodecene compound of the following general formula (3):

$$CH_3CH_2=CH(CH_2)_7CH(OR)_2 \quad (3)$$

in which R is as defined above; and
hydrolyzing the 1,1-dialkoxy-9-dodecene compound (3) thus obtained to produce the 9-dodecenal compound (4).

Alternatively, According to another aspect of the present invention, there is provided a process for preparing a 9-dodecenal compound of the following formula (4):

$$CH_3CH_2CH=CH(CH_2)_7CHO \quad (4)$$

the process comprising steps of
preparing a nucleophilic reagent, 8-undecenyl compound, of the following general formula (1)

$$CH_3CH_2CH=CH(CH_2)_7M^1 \quad (1)$$

in which $M^1$ represents Li or $MgZ^1$, wherein $Z^1$ represents a halogen atom or an 8-undecenyl group
from an 11-halo-3-undecene compound of the following general formula (7):

$$CH_3CH_2CH=CH(CH_2)_7X^1 \quad (7)$$

in which $X^1$ represents a halogen atom;
subjecting, the nucleophilic reagent, 8-undecenyl compound (1) thus obtained, to a nucleophilic substitution reaction with an orthoformic ester compound of the following general formula (2):

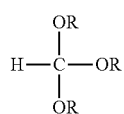

(2)

in which R may be same with or different from each other and represents an alkyl group having 1 to 6 carbon atoms,
to produce a 1,1-dialkoxy-9-dodecene compound of the following general formula (3):

$$CH_3CH_2CH=CH(CH_2)_7CH(OR)_2 \quad (3)$$

in which R is as defined above; and
hydrolyzing the 1,1-dialkoxy-9-dodecene compound (3) thus obtained to produce the 9-dodecenal compound (4).

According to another aspect of the present invention, there is provided an 11-halo-3-undecene compound of the following general formula (7):

$$CH_3CH_2CH=CH(CH_2)_7X^1 \quad (7)$$

in which $X^1$ represents a halogen atom.
The 11-halo-3-undecene compound (7) of the present invention is useful in producing the 9-dodecenal compound (4).

According to the present invention, the 9-dodecenal compound (4) can be prepared in a high yield without an oxidation reaction.

DETAILED DESCRIPTION OF THE INVENTION

First, the 11-halo-3-undecene compound (7) will be explained, which is a raw material in the preparation of the nucleophilic reagent, 8-undecenyl compound (1).

The 11-halo-3-undecene compound (7) may be produced by subjecting a nucleophilic reagent, 3-hexenyl compound, of the following general formula (5) to a coupling reaction with a 1-halo-5-halopentane compound of the following general formula (6) to produce the 11-halo-3-undecene compound (7), as shown in the following chemical reaction formula.

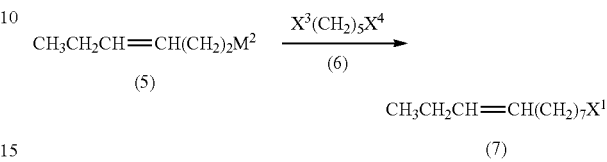

$M^2$ in the nucleophilic reagent, 3-hexenyl compound (5), represents Li or $MgZ^2$, wherein $Z^2$ represents a halogen atom or a 3-hexenyl group. Examples of the halogen atom, $Z^2$, include a chlorine atom, a bromine atom, and an iodine atom.

Examples of the nucleophilic reagent, 3-hexenyl compound (5), include a nucleophilic reagent, (3E)-3-hexenyl compound of foe following general formula (5-1), a nucleophilic reagent, (3Z)-3-hexenyl compound of the following general formula (5-2), and a mixture thereof.

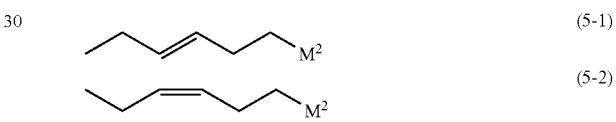

Examples of the nucleophilic reagent, (3E)-3-hexenyl compound (5-1), include (3E)-3-hexenyl lithium; and (3E)-3-hexenylmagnesium halide reagent (Grignard reagent) such as (3E)-3-hexenylmagnesium chloride, (3E)-3-hexenylmagnesium bromide and (3E)-3-hexenylmagnesium iodide, with (3E)-3-hexenylmagnesium halide reagent being preferred in view of the versatility.

Examples of the nucleophilic reagent, (3Z)-3-hexenyl compound (5-2), include (3Z)-3-hexenyl lithium; and (3Z)-3-hexenylmagnesium halide reagent (Grignard reagent) such as (3Z)-3-hexenylmagnesium chloride, (3Z)-3-hexenylmagnesium bromide and (3Z)-3-hexenylmagnesium iodide with (3Z)-3-hexenylmagnesium halide reagent being preferred in view of the versatility.

The nucleophilic reagent, 3-hexenyl compound (5), may be used either alone or in combination thereof.

For instance, a mixture of the (3E)-11-halo-3-undecene compound and the (3Z)-11-halo-3-undecene compound is synthesized from a mixture of the nucleophilic reagent: (3E)-3-hexenyl compound (5-1), and the nucleophilic reagent: (3Z)-3-hexenyl compound (5-2).

The nucleophilic reagent, 3-hexenyl compound (5), may be commercially available one or may be synthesized in house.

The nucleophilic reagent, 3-hexenyl compound (5), can be prepared from a 1-halo-3-hexene compound (8), as shown in the following chemical reaction formula.

For instance, the 3-hexenylmagnesium halide (5: $M^2=MgZ^2$) such as the (3E)-3-hexenylmagnesium halide and the (3Z)-3-hexenylmagnesium halide may be produced by reacting the 1-halo-3-hexene compound (8) with magnesium in a solvent to produce the 3-hexenylmagnesium halide (5: $M^2=MgZ^2$), as shown in the following chemical reaction formula.

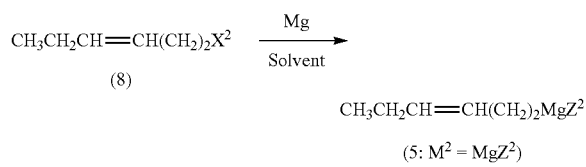

$X^2$ in the 1-halo-3-hexene compound (8) represents a halogen atom. Examples of the halogen atom, $X^2$, include a chlorine atom, a bromine atom, and an iodine atom.

Examples of the 1-halo-3-hexene compound (8) include (3E)-1-halo-3-hexene compound of the following general formula (8-1), (3Z)-1-halo-3-hexene compound of the following general formula (8-2), and a mixture thereof.

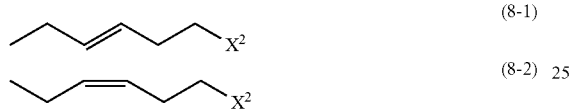

Examples of the (3E)-1-halo-3-hexene compound (8-1) include (3E)-1-chloro-3-hexene, (3E)-1-bromo-3-hexene, and (3E)-1-iodo-3-hexene.

Examples of the (3Z)-1-halo-3-hexene compound (8-2) include (3Z)-1-chloro-3-hexene, (3Z)-1-bromo-3-hexene, and (3Z)-1-iodo-3-hexene.

The 1-halo-3-hexene compound (8) may be used either alone or in combination thereof.

For instance, a mixture of the nucleophilic reagent: (3E)-3-hexenyl compound (5-1), and the nucleophilic reagent: (3Z)-3-hexenyl compound (5-2), is synthesized from a mixture of the nucleophilic reagent: (3E)-1-halo-3-hexene compound (8-1), and the nucleophilic reagent: (3Z)-1-halo-3-hexene compound (8-2).

The 1-halo-3-hexene compound (8) may be commercially available one or may be synthesized in house.

An amount of magnesium to be used in preparing the 3-hexenylmagnesium halide (5: $M^2=MgZ^2$) from the 1-halo-3-hexene compound (8) is preferably from 1.0 to 2.0 gram atoms per mol of the 1-halo-3-hexene compound (8) in view of the completion of the reaction.

Examples of the solvent to be used in preparing the 3-hexenylmagnesium halide (5: $M^2=MgZ^2$) from the 1-halo-3-hexene compound (8) include ether solvents such as tetrahydrofuran, diethyl ether and 4-methyltetrahydropyran; and hydrocarbon solvents such as toluene, xylene and hexane. Tetrahydrofuran is preferred in view of a reaction rate in the formation of the Grignard reagent.

The solvent may be used either alone or in combination thereof. The solvent may be commercially available one or may be synthesized in house.

An amount of the solvent is preferably from 100 to 2000 g per mol of the 1-halo-3-hexene compound (8) in view of the reactivity.

A reaction temperature in preparing the 3-hexenylmagnesium halide (5: $M^2=MgZ^2$) from the 1-halo-3-hexene compound (8) varies, depending cm a solvent used, and is preferably from 30 to 120 in view of the reactivity.

A reaction time in preparing foe 3-hexenylmagnesium halide (5: $M^2=MgZ^2$) from the 1-halo-3-hexene compound (8) varies, depending on a solvent used or a production scale, and is preferably from 1 to 50 hours in view of the reactivity.

For instance, the 3-hexenyl lithium reagent (5: $M^2=Li$) such as (3E)-3-hexenyl lithium and (3Z)-3-hexenyl lithium may be produced by reacting the 1-halo-3-hexene compound (8) with an organic lithium reagent in a solvent to produce the 3-hexenyl lithium reagent (5: $M^2=Li$), as shown in the following chemical reaction formula.

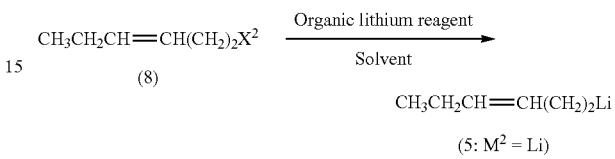

Examples of the organic lithium reagent include linear organic lithium reagents such as methyllithium, ethyllithium, n-propyllithium, n-butyllithium and n-pentyllithium; and branched organic lithium reagents such as sec-butyllithium and tert-butyllithium. Methyllithium, n-butyllithium, sec-butyllithium and tert-butyllithium are preferred in view of the versatility.

An amount of the organic lithium reagent is preferably from 1.0 to 4.0 mol per mol of the 1-halo-3-hexene compound (8) in view of the reactivity.

Examples of the solvent to be used in preparing the 3-hexenyl lithium reagent (5: $M^2=Li$) from the 1-halo-3-hexene compound (8) include ether solvents such as tetrahydrofuran, diethyl ether and 4-methyltetrahydropyran; and hydrocarbon solvents such as toluene, xylene and hexane. A preferred solvent varies, depending on an organic lithium reagent used, and is generally preferably tetrahydrofuran, toluene and hexane in view of the reactivity.

The solvent may be used either alone or in combination thereof. The solvent may be commercially available one or may be synthesized in house.

An amount of the solvent is preferably from 50 to 5000 g per mol of the 1-halo-3-hexene compound (8) in view of the reactivity.

N,N,N',N'-tetramethylethylenediamine (TMEDA), hexamethylphosphoric triamide (HMPA) and N,N'-dimethylpropylene urea (DMPU) may be added to improve a reaction rate when the 3-hexenyl lithium reagent (5: $M^2=Li$) is prepared from the 1-halo-3-hexene compound (8).

A reaction temperature in preparing the 3-hexenylmagnesium halide (5: $M^2=Li$) from the 1-halo-3-hexene compound (8) varies, depending on a solvent used, and is preferably from −78 to 25° C. in view of the reactivity.

A reaction time in preparing the 3-hexenyl lithium reagent (5: $M^2=Li$) from the 1-halo-3-hexene compound (8) varies, depending on a solvent used or a production scale, and is preferably from 1 to 50 hours in view of the reactivity.

An amount of the nucleophilic reagent, 3-hexenyl compound (5), in the aforesaid coupling reaction is preferably from 0.8 to 1.4 mol per mol of the 1-halo-5-halopentane compound (6) in view of the economy.

$X^3$ and $X^4$ in the 1-halo-5-halopentane compound (6) may be same with or different from each other and represents a halogen atom. Examples of the halogen atom, $X^3$ and $X^4$, include a chlorine atom, a bromine atom, and an iodine atom.

Examples of a combination of $X^3$ and $X^4$ include a chlorine atom with a chlorine atom, a bromine atom with a chlorine atom, a chlorine atom with an iodine atom, a bromine atom with a bromine atom, a bromine atom with an iodine atom, and an iodine atom with an iodine atom.

Examples of the 1-halo-5-halopentane compound (6) include 1,5-dichloropentane, 1-bromo-5-chloropentane, 1-chloro-5-iodopentane, 1,5-dibromopentane, 1-bromo-5-iodopentane, and 1,5-diiodopentane.

The 1-halo-5-halopentane compound (6) may be used either alone or in combination thereof. The 1-halo-5-halopentane compound (6) may be commercially available one or may be synthesized in house.

In a case where $X^3$ and $X^4$ differ from each other, the coupling reaction may proceed with preference of a halogen atom having a higher reactivity, by appropriately selecting a catalyst or a reaction temperature, as will be explained below, with a combination of $X^3$ and $X^4$ which are different from each other being preferred in the coupling reaction. For instance, $X^1$ in the 11-halo-3-undecene compound (7) will become a chlorine atom by the use of the 1-halo-5-halopentane compound (6) which has a combination of $X^3$ and $X^4$: a chlorine atom with a bromine atom or a chlorine atom with an iodine atom. $X^1$ in the 11-halo-3-undecene compound (7) will become a bromine atom by the use of the 1-halo-5-halopentane compound (6) which has a combination of $X^3$ and $X^4$: a bromine atom with an iodine atom.

A solvent may be used in the coupling reaction, if necessary. Examples of the solves include hydrocarbon solvents such as toluene, xylene and hexane; ether solvents such as tetrahydrofuran, 4-methyltetrahydropyran and diethyl ether, and polar solvents such as N,N-dimethylformamide, N,N-dimethylacetamide, N-methylpyrrolidone, dimethyl sulfoxide, γ-butyrolactone and acetonitrile. Toluene, tetrahydrofuran, 4-methyltetrahydropyran and acetonitrile are preferred, with tetrahydrofuran being more preferred, in view of the reactivity.

The solvent may be used either alone or in combination thereof. The solvent may be commercially available one or may be synthesized in house.

An amount of the solvent is preferably from 30 to 3000 g per mol of the 1-halo-5-halopentane compound (6) in view of the reactivity.

A catalyst may be used in the coupling reaction, if necessary. Examples of the catalyst include cuprous halides such as cuprous chloride, cuprous bromide, and cuprous iodide; and cupric halides such as cupric chloride, cupric bromide, and cupric iodide, with cuprous halides being preferred, and with cuprous iodide being more preferred, in view of the reactivity.

The catalysts may be used either alone or in combination thereof. The catalyst may be commercially available one.

An amount of the catalyst is preferably from 0.003 to 0.300 mol per mol of the 1-halo-5-halopentane compound (6) in view of a reaction rate and easy post-processing.

When the catalyst is used in the colliding reaction, a cocatalyst may also be used, if necessary. Examples of the cocatalyst include trialkyl phosphite compounds having 3 to 9 carbon atoms, such as triethyl phosphite; and phosphorus compounds, such as triarylphosphine compounds having 18 to 21 carbon atoms, such as triphenylphosphine, with triethyl phosphite being preferred in view of foe reactivity.

The cocatalyst may be used either alone or in combination thereof. The cocatalyst may be commercially available one.

An amount of the cocatalyst is preferably hum 0.001 to 0.500 mol, more preferably firm 0.001 to 0.050 mol, per mol of the 1-halo-5-halopentane compound (6).

In a case where the catalyst is used in the foe coupling reaction, lithium halide may be added, if necessary. Examples of the lithium halide include lithium chloride, lithium bromide and lithium iodide, with lithium chloride being preferred in view of the reactivity.

An amount of the lithium halide in the coupling reaction is preferably hum 0.005 to 0.250 mol per mol of the 1-halo-5-halopentane compound (6) in view of the reactivity.

A reaction temperature in the coupling reaction varies, depending on the a nucleophilic reagent, 3-hexenyl compound (5), used, and is preferably from −78 to 70° C., more preferably −20 to 25° C., in view of the reactivity.

A reaction time in the coupling reaction varies, depending on a solvent used or a production scale, and is preferably hum 1 to 55 hours in view of the reactivity.

Examples of the 11-halo-3-undecene compound (7) include a (3E)-11-halo-3-undecene compound of the following general formula (7-1), a (3Z)-11-halo-3-undecene compound of the following general formula (7-2), and a mixture thereof.

(7-1)

(7-2)

$X^1$ in the 11-halo-3-undecene compound (7) represents a halogen atom. Examples of the halogen atom, $X^1$, include a chlorine atom, a bromine atom, and an iodine atom, with a chlorine atom and a bromine atom being preferred in view of the reactivity.

Examples of the (3E)-11-halo-3-undecene compound (7-1) include (3E)-11-chloro-3-undecene, (3E)-11-bromo-3-undecene, and (3E)-11-iodo-3-undecene.

Examples of the (3Z)-11-halo-3-undecene compound (7-2) include (3Z)-11-chloro-3-undecene, (3Z)-11-bromo-3-undecene, and (3Z)-11-iodo-3-undecene.

Next, a process for preparing the 1,1-dialkoxy-9-dodecene compound (3) will be explained below, which process Is a part of a process for preparing the 9-dodecenal compound (4). The process comprises a step of subjecting a nucleophilic reagent, 8-undecenyl compound, of the following general formula (1) and an orthoformic ester compound of the following general formula (2) to a nucleophilic substitution reaction to produce foe 1,1-dialkoxy-9-dodecene (3).

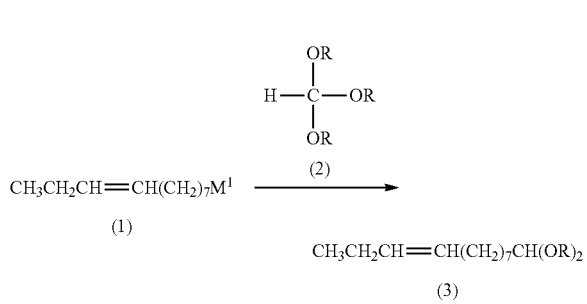

$M^1$ in the nucleophilic reagent, 8-undecenyl compound (1), represents Li or $MgZ^1$, wherein $Z^1$ represents a halogen atom or an 8-undecenyl group. Examples of foe halogen atom, $Z^1$, include a chlorine atom, a bromine atom, and an iodine atom.

Examples of the nucleophilic reagent, 8-undecenyl compound (1), include (8E)-8-undecenyl compound of the following formula (1-1), (8Z)-8-undecenyl compound of the following formula (1-2), and a mixture thereof.

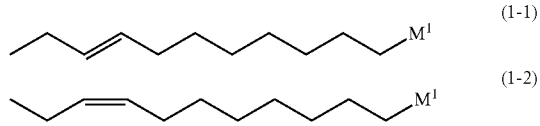

Examples of foe nucleophilic reagent, (8E)-8-undecenyl compound (1-1), includes (8E)-8-undecenyllithium; and an (8E)-8-undecenylmagnesium halide reagent (Grignard reagent) such as (8E)-8-undecenylmagnesium chloride, (8E)-8-undecenylmagnesium bromide and (8E)-8-undecenylmagnesium iodide, with (8E)-8-undecenylmagnesium halide being preferred in view of the versatility.

Examples of the nucleophilic reagent, (8Z)-8-undecenyl compound (1-2), includes (8Z)-8-undecenyllithium; and an (8Z)-8-undecenylmagnesium halide reagent (Grignard reagent) such as (8Z)-8-undecenylmagnesium chloride, (8Z)-8-undecenylmagnesium bromide and (8Z)-8-undecenylmagnesium iodide, with (8Z)-8-undecenylmagnesium halide being preferred in view of the versatility.

The nucleophilic reagent, 8-undecenyl compound (1), may be used either alone or in combination thereof.

For instance, a mixture of the (9E)-1,1-dialkoxy-9-dodecene compound and the (9Z)-1,1-dialkoxy-9-dodecene compound is synthesized from a mixture of tire nucleophilic reagent: (8K)-8-undecenyl compound (1-1), and the nucleophilic reagent: (8Z)-8-undecenyl compound (1-2), as the nucleophilic reagent, 8-undecenyl compound (1).

The nucleophilic reagent, 8-undecenyl compound (1), may be synthesized in house.

The nucleophilic reagent, 8-undecenyl compound (1), may be prepared from the 11-halo-3-undecene compound (7).

For instance, the 8-undecenylmagnesium halide reagent (1: $M^1=MgX^1$), such as the (8E)-8-undecenylmagnesium halide reagent and the (8Z)-8-undecenylmagnesium halide reagent, may be produced by reacting the 11-halo-3-undecene compound (7) with magnesium in a solvent, as shown in the following chemical reaction formula.

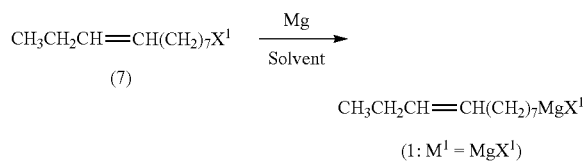

The 11-halo-3-undecene compound (7) may be used either alone or in combination thereof.

For instance, a mixture of the nucleophilic reagent, (8E)-8-undecenyl compound, and the nucleophilic reagent, (8Z)-8-undecenyl compound, may be synthesized from a mixture of the (3E)-11-halo-3-undecene compound and the (3Z)-11-halo-3-undecene compound.

An amount of magnesium to be used in preparing the 8-undecenylmagnesium halide reagent (1: $M^1=MgX^1$) from the 11-halo-3-undecene compound (7) is preferably from 1.0 to 2.0 gram atoms per mol of the 11-halo-3-undecene compound (7) in view of the completion of the reaction.

Examples of the solvent include ether solvents such as tetrahydrofuran, diethyl ether and 4-methyltetrahydropyran; and hydrocarbon solvents such as toluene, xylene and hexane. Tetrahydrofuran is preferred in view of a reaction rate in the formation of the Grignard reagent.

An amount of the solvent is preferably hum 100 to 2000 g per mol of the 11-halo-3-undecene compound (7) in view of the reactivity.

A reaction temperature in preparing the 8-undecenylmagnesium halide reagent (1: $M^1=MgX^1$) from the 11-halo-3-undecene compound (7) varies, depending on a solvent used, and is preferably from 30 to 120° C. in view of the reactivity.

A reaction time in preparing the 8-undecenylmagnesium halide reagent (1: $M^1=MgX^1$) from the 11-halo-3-undecene compound (7) varies, depending on a solvent used or a production scale, and is preferably from 1 to 50 hours in view of the reactivity.

For instance, the (8E)-8-undecenyllithium reagent (1: $M^1=Li$), such as (8E)-8-undecenyllithium, and (8Z)-8-undecenyllithium may be produced by reacting the 11-halo-3-undecene compound (7) will an organic lithium reagent in a solvent to produce the (8E)-8-undecenyllithium reagent (1: $M^1=Li$), as shown in the following chemical reaction formula.

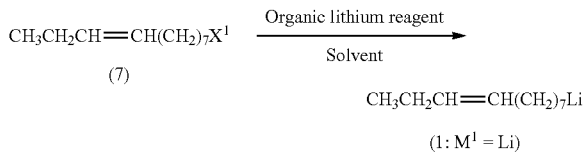

Examples of fee organic lithium reagent include a linear organic lithium reagent such as methyllithium, ethyllithium, n-propyllithium, n-butyllithium and n-pentyllithium; and a branched organic lithium reagent such as sec-butyllithium and tert-butyllithium. Methyllithium, n-butyllithium, sec-butyllithium and tert-butyllithium are preferred in view of the versatility.

An amount of the organic lithium reagent is preferably from 1.0 to 4.0 mol per mol of the 11-halo-3-undecene compound (7) in view of the reactivity.

Examples of the solvent to be used in preparing the (8E)-8-undecenyllithium reagent (1: $M^1=Li$) from the 11-halo-3-undecene compound (7) include ether solvents such as tetrahydrofuran, diethyl ether and 4-methyltetrahydropyran; and hydrocarbon solvents such as toluene, xylene and hexane. A preferred solvent varies, depending on an organic lithium reagent used, and is generally tetrahydrofuran, toluene and hexane generally in view of the reactivity.

The solvent may be used either alone or in combination thereof. The solvent may be commercially available one or may be synthesized in house.

An amount of the solvent is preferably from 50 to 5000 g per mol of the 11-halo-3-undecene compound (7) in view of the reactivity.

N,N,N',N'-tetramethylethylenediamine (TMEDA), hexamethylphosphoric triamide (HMPA) and N,N'-dimethylpropylene urea (DMPU) may be added to improve a reaction rate when the (8E)-8-undecenyllithium reagent (1: $M^1=Li$) is prepared from the 11-halo-3-undecene compound (7).

A reaction temperature in preparing the (8E)-8-undecenyllithium reagent (1: $M^1=Li$) from the 11-halo-3-undecene compound (7) varies, depending on a solvent used, and is preferably from −78 to 25° C. in view of the reactivity.

A reaction time in preparing the (8E)-8-undecenyllithium reagent (1: M¹=Li) from the 11-halo-3-undecene compound (7) varies, depending on a solvent used or a production scale, and is preferably from 1 to 50 hours in view of the reactivity.

An amount of the nucleophilic reagent, 8-undecenyl compound (1), is preferably from 0.5 to 1.5 mol per mol of the orthoformic ester compound (2) in view of the economy.

Three Rs in the ortho formic ester compound (2) may be same with or different from each other and represent an alkyl group having 1 to 6, preferably 1 to 3, carbon atoms.

Examples of the alkyl group having 1 to 6 carbon atoms include a linear alkyl group such as a methyl group, an ethyl group, an n-propyl group, an n-butyl group, an n-pentyl group and an n-hexyl group; and a branched alkyl group such as an isopropyl group and an isobutyl group.

Examples of the orthoformic ester compound (2) include methyl orthoformate, ethyl orthoformate, propyl orthoformate, butyl orthoformate, pentyl orthoformate and hexyl orthoformate, with methyl orthoformate and ethyl orthoformate being preferred in view of availability.

The orthoformic ester compound (2) may be used either alone or in combination thereof. The orthoformic ester compound (2) may be commercially available one.

Examples of the solvent used in the nucleophilic substitution reaction include hydrocarbon solvents such as toluene, xylene and hexane; and ether solvents such as tetrahydrofuran, 4-methyltetrahydropyran and diethyl ether. Toluene and 4-methyltetrahydropyran are preferred in view of the reactivity.

The solvent may be used either alone or in combination thereof. The solvent may be commercially available one.

When the nucleophilic reagent, 8-undecenyl compound (1), is diluted with a solvent, or when a solvent was used to prepare the nucleophilic reagent, 8-undecenyl compound (1), these solvents and the solvents used in the nucleophilic substitution reaction may be same with or different from each other.

In a case where the solvents are different from each other, a solvent may be replaced with a solvent which increases the reactivity of the nucleophilic substitution reaction.

For instance, in a case where tetrahydrofuran was used in preparing the nucleophilic reagent, 8-undecenyl compound (1), and toluene is selected as a solvent for the nucleophilic substitution reaction, the nucleophilic reagent, 8-undecenyl compound (1), containing tetrahydrofuran is added to a reactor containing the orthoformic ester compound and toluene, and tetrahydrofuran is distilled off in a course of raising a reaction temperature, so that a solvent may be replaced with toluene in the reaction system.

An amount of the solvent is preferably from 100 to 6000 g per mol of the orthoformic ester compound (2) in view of the reactivity.

A reaction temperature in the nucleophilic substitution reaction is preferably from 75 to 130° C. in view to smoothly proceed with the reaction and prevent evaporation of the solvent.

A reaction time in the nucleophilic substitution reaction varies, depending on a solvent used or a production scale, and is preferably from 1 to 100 hours.

Examples of the 1,1-dialkoxy-9-dodecene compound (3) include a (9E)-1,1-dialkoxy-9-dodecene compound of the following general formula (3-1), a (97)-1,1-dialkoxy-9-dodecene compound of the following general formula (3-1), and a mixture thereof.

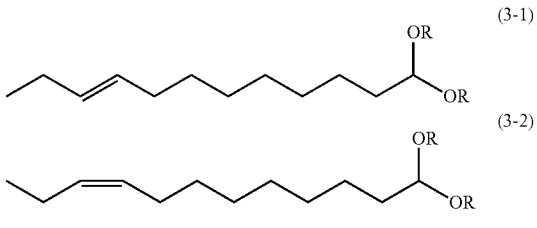

R in the 1,1-dialkoxy-9-dodecene compound (3) is same with R in the orthoformic ester compound (2).

Examples of the (9E)-1,1-dialkoxy-9-dodecene compound (3-1) include (9E)-1,1-dimethoxy-9-dodecene, (9E)-1,1-diethoxy-9-dodecene, (9E)-1,1-dipropoxy-9-dodecene and (9E)-1,1-dibutoxy-9-dodecene.

Examples of the (9Z)-1,1-dialkoxy-9-dodecene compound (3-2) include (9Z)-1,1-dimethoxy-9-dodecene, (9Z)-1,1-diethoxy-9-dodecene, (9Z)-1,1-dipropoxy-9-dodecene and (9Z)-1,1-dibutoxy-9-dodecene.

Next a process for preparing the 9-dodecenal compound (4) will be explained below, which process is a part of a process for preparing the 9-dodecenal compound (4). The process comprises a step of hydrolyzing the 1,1-dialkoxy-9-dodecene compound (3) to produce the 9-dodecenal compound (4).

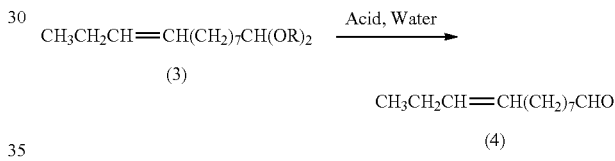

The 1,1-dialkoxy-9-dodecene compound (3) may be used either alone or in combination thereof.

For instance, a mixture of (9E)-9-dodecenal and (9Z)-9-dodecenal may be synthesized from a mixture of the (9E)-1,1-dialkoxy-9-dodecene compound and the (9Z)-1,1-dialkoxy-9-dodecene compound.

The hydrolysis may be earned out, using, for example, an add, water and, if necessary, a solvent.

Examples of the add used in the hydrolysis include inorganic acids such as hydrochloric acid and hydrobromic acid; p-toluenesulfonic add, trifluoroacetic acid, acetic acid, formic acid, oxalic acid, iodotrimethylsilane and titanium tetrachloride, with acetic acid, formic add and oxalic acid bring preferred in view of the reactivity.

The acid may be used either alone or in combination thereof. The adds may be commercially available one.

An amount of the acid used is preferably 0.01 to 10.0 mol per mol of the 1,1-dialkoxy-9-dodecene compound (3).

An amount of water used in the hydrolysis is preferably from 18 to 3,000 g per mol of the 1,1-dialkoxy-9-dodecene compound (3).

Examples of the solvent used in the hydrolysis include hydrocarbon solvents such as toluene, xylene and hexane; ether solvents such as tetrahydrofuran and diethyl ether, polar solvents such as N,N-dimethylformamide, N,N-dimethylacetamide, N-methylpyrolidone, acetonitrile, γ-butyrolactone, dichloromethane and chloroform; and alcohols such as methanol and ethanol.

The solvent may be used either alone or in combination thereof. The solvent may be commercially available one.

An optimum solvent varies, depending on an acid used. For instance, when oxalic add is used as the acid, tetrahydrofuran is preferred in view of the reactivity.

An amount of the solvent is preferably from 0 to 3000 g per mol of the 1,1-dialkoxy-9-dodecene compound (3) in view of the reactivity.

A reaction temperature in the hydrolysis varies, depending on an acid or solvent used, and is preferably from 5 to 180° C. in view of the reactivity.

A reaction time in the hydrolysis varies, depending on a solvent used or a production scale, and is preferably from 1 to 55 hours in view of the reactivity.

Examples of the 9-dodecenal compound (4) include (9E)-9-dodecenal of the following formula (4-1), (9Z)-9-dodecenal of the following formula (4-2), and a mixture thereof.

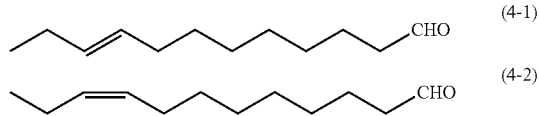

EXAMPLE

The present invention will be further described with reference to the following Examples. It should be understood that the present invention is not limited to or by the Examples.

The term "purity" as used herein means a percentage of an area obtained by gas chromatography (GC), unless otherwise specified. The term "production ratio" means a ratio of percentages of areas obtained by GC. The yield is calculated from the area percentages obtained by GC.

In the Examples, monitoring of the reactions and calculation of the yields carried out in the following GC conditions.

<GC conditions>: Capillary gas chromatograph GC-2014, ex Shimadzu Corporation; column: DB-5, 0.25 μm×0.25 mmφ×30 m; carrier gas: He (1.55 mL/min); detector: FID; column temperature: 150° C., elevated by 5° C./min, up to 230° C.

The yield was calculated by the following equation in consideration of purities (% GC) of a starting material and a product.

Yield (%)={[(weight of a product obtained by a reaction×% GC)/molecular weight of a product] ÷[(weight of a starting material in a reaction×% GC)/molecular weight of a starting material]}×100

Example 1

Preparation of (3Z)-11-chloro-3-undecene (7-2: $X^1$=Cl)

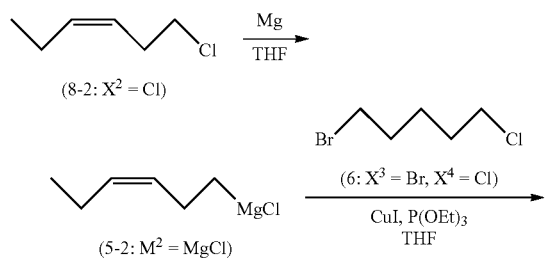

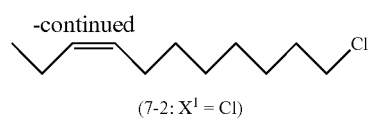

Magnesium (114.82 g, 4.73 gram atoms) and tetrahydrofuran (1350 g) were placed in a reactor at room temperature and stirred at from 60 to 65° C. for 20 minutes. Then, (3Z)-1-chloro-3-hexene (8-2: $X^2$=Cl) (533.70 g, 4.50 mol) was added dropwise to the reactor at from 60 to 75° C. After the completion of the dropwise addition, the reaction mixture was stirred at from 75 to 80° C. for 2 hours to form (3Z)-3-hexenylmagnesium chloride (5-2: $M^2$=MgCl).

Next, cuprous iodide (8.57 g, 0.045 mol), triethyl phosphite (17.95 g, 0.11 md), tetrahydrofuran (450 g) and 1-bromo-5-chloropentane (6: $X^3$=Br, $X^4$=Cl) (776.28 g, 4.19 mol) were placed in another reactor. Then, (3Z)-3-hexenylmagnesium chloride (5-2: $M^2$=MgCl) obtained above was added dropwise at from −5 to 15° C. After the completion of the dropwise addition, stirring was continued at from 5 to 15° C. for 3.5 hours. Then, a mixture of acetic acid (562.50 g) and water (1687.50 g) was added to the reaction mixture, Mowed by phase separation and removal of the aqueous phase. Then, the organic phase was concentrated at a reduced pressure and the residue was subjected to distillation at a reduced pressure to obtain (3Z)-11-chloro-3-undecene (7-2: $X^1$=Cl) (740.43 g, 3.92 mol, purity: 100%) in a yield of 93.75%.

The following are spectrum data of (3Z)-11-chloro-3-undecene (7-2: $X^1$=Cl) thus produced.

[Nuclear magnetic resonance spectrum] $^1$H-NMR (500 MHz CDCl$_3$): δ 0.95 (3H, t, J=7.6 Hz), 128-138 (6H, m), 1.39-1.46 (2H, m), 1.77 (2H, tt-like), J=73 Hz), 1.99-207 (4H, m), 3.53 (2H, t, J=6.7 Hz), 5.28-5.40 (2H, m); $^{13}$C-NMR (125 MHz, CDCl$_3$): δ 14.37, 20.50, 26.84, 27.00, 28.76, 29.04, 29.60, 32.62, 45.13, 129.12, 131.64

[Mass spectrum] EI-Mass spectrum (70 eV): m/z 188 (M$^+$), 104, 83, 69, 55, 41, 27

[Infrared absorption spectrum] (NaCl): ν=2961, 2930, 2856, 1463, 726, 654

Example 2

Preparation of (3E)-11-chloro-3-undecene (7-1: $X^1$=Cl)

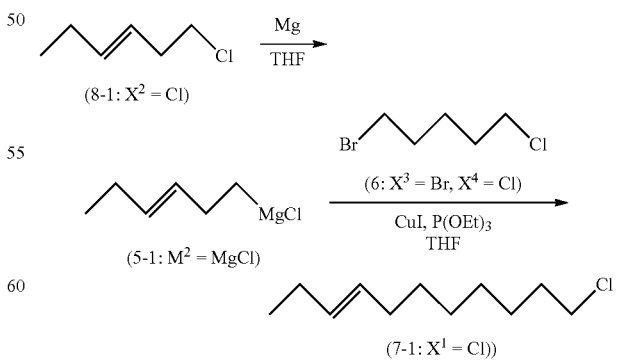

Magnesium (54.91 g, 2.26 g atoms) and tetrahydrofuran (645.60 g) were placed in a reactor at room temperature and stirred at from 60 to 65° C. for 25 minutes. Then. (3E)-1- chloro-3-hexene (8-1: $X^2$=Cl)(255.23 g, 2.15 mol) was added dropwise to the reactor at from 60 to 75° C. After the completion of the drop wise addition, the reaction mixture was stirred at from 75 to 80° C. for 2 hours to form (3E)-3-hexenylmagnesium chloride (5-1: $M^2$=MgCl).

Next, cuprous iodide (4.10 g, 0.022 mol), triethyl phosphite (8.58 g, 0.052 mol), tetrahydrofuran (215.20 g) and 1-bromo-5-chloropentane (6: $X^3$=Br; $X^4$=Q) (37123 g, 2.00 mol) were placed in another reactor. Then, (3E)-3-hexenylmagnesium chloride obtained above was added dropwise at from −5 to 15° C. After the completion of the dropwise addition, stirring was continued at from 5 to 15° C. far 3 hours. Then, a mixture of acetic add (269.00 g) and water (807.00 g) was added to the reaction mixture, followed by phase separation and removal of the aqueous phase. Then, the organic phase was concentrated at a reduced pressure and the residue was subjected to distillation at a reduced pressure to obtain (3E)-11-chloro-3-undecene (7-1: $X^1$=Cl) (341.43 g, 1.81 mol, purity: 100%) in a yield of 90.40%.

The following are spectrum data of (3E)-11-chloro-3-undecene (7-1: $X^1$=Cl) thus produced.

[Nuclear magnetic resonance spectrum] $^1$H-NMR (500 MHz CDCl$_3$): δ0.96 (3H, t, J=7.5 Hz), 1.27-138 (6H, m), 1.38-1.46 (2H, m), 1.76 (2H, tt, J=7.3 Hz; 7.3 Hz), 1.94-2.03 (4H, m), 3.53 (2H, t, J=6.9 Hz), 5.38 (1H, dt, J=15.2 Hz, 6.2 Hz), 5.44 (1H, dt, J=15.2 Hz, 6.1 Hz); $^{13}$C-NMR (125 MHz, CDCl$_3$): δ 13.97, 25.38, 26.83, 28.74, 28.93, 29.49, 32.48, 32.62, 45.14, 129.17, 132.00

[Mass spectrum] EI-Mass spectrum (70 eV): m/z 188 (M$^+$), 104, 83, 69, 55, 41, 27

[Infrared absorption spectrum] (NaCl): ν=2960, 2928, 2855, 1462, 966, 726, 654

Example 3

Preparation of (9Z)-1,1-diethoxy-9-dodecene (3-2: R=Et)

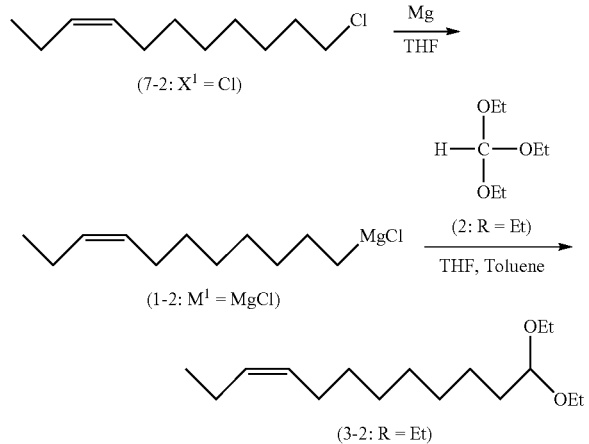

Magnesium (73.99 g, 3.05 mol) and tetrahydrofuran (870.00 g) were placed in a reactor at room temperature and stirred al from 60 to 65° C. for 20 minutes. Then, (3Z)-11-chloro-3-undecane (7-2: $X^1$=Cl) (547.35 g, 2.90 mol) was added dropwise to the reactor at from 60 to 75° C. After the completion of the dropwise addition, the reaction mixture was stirred at from 75 to 80° C. for 2.5 hours to form (8Z)-8-undecenylmagnesium chloride (1-2: $M^1$=MgCl).

Next, toluene (1348.50 g) and ethyl orthoformate (2: R=Et) (558.71 g, 3.77 mol) were added dropwise to the reactor at from 75 to 85° C. After the completion of the dropwise addition, stirring was continued at from 90 to 100° C. for 16 hours. Then, the reaction mixture was cooled to a temperature of 30 to 45° C. Then, a mixture of acetic acid (362.50 g) and water (1087.50 g) were added to the reactor, followed by phase separation and removal of the aqueous phase. Then, the organic phase was concentrated at a reduced pressure and the residue was subjected to distillation at a reduced pressure to obtain a crude product, (9Z)-1,1-diethoxy-9-dodecene (3-2: R=Et), (641.06 g, 2.34 mol, purity: 93.65%) in a crude yield of 80.73%.

The following are spectrum data of (9Z)-1,1-diethoxy-9-dodecene (3-2: R=Et) thus produced.

[Nuclear magnetic resonance spectrum] $^1$H-NMR (500 MHz CDCl$_3$): δ 0.94 (3H, t, J=7.5 Hz), 1.19 (6H, t, J=7.1 Hz), 1.24-1.37 (10H, m), 1.59 (2H, dt, J=9.2 Hz, 6.0 Hz), 2.01 (4H, sext-like, J=72 Hz), 3.47 (2H, dq, J=7.1 Hz, 82 Hz), 3.62 (2H, dq, J=7.1 Hz, 82 Hz), 4.46 (1H, t, J=5.8 Hz), 5.27-5.38 (2H, m); $^{13}$C-NMR (125 MHz, CDCl$_3$): δ 14.35, 15.32, 20.47, 24.71, 27.03, 29.15, 29.41, 29.70, 33.54, 60.75, 102.92, 129 24, 131.48

[Mass spectrum] EI-Mass spectrum (70 eV): m/z 211 (M$^+$-45), 103, 75, 47, 29

[Infrared absorption spectrum] (NaCl): ν=2973, 2927, 2855, 1463, 1373, 1344, 1127, 1064, 723

Example 4

Preparation of (9E)-1,1-diethoxy-9-dodecene (3-1: R=Et)

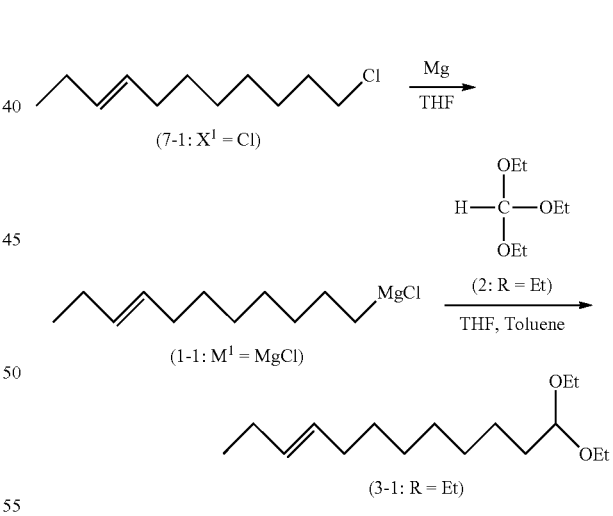

Magnesium (35.93 g, 1.48 mol) and tetrahydrofuran (422.40 g) were placed in a reactor at room temperature and stirred at from 60 to 65° C. for 16 minutes. Then, (3E)-11-chloro-3-undecene (7-1: $X^1$=Cl) (265.75 g, 1.41 mol) was added dropwise to the reactor at from 60 to 75° C. After the completion of the dropwise addition, the reaction mixture was stirred at from 75 to 80° C. for 3 hours to form (8E)-8-undecenylmagnesium chloride (1-1: $M^1$=MgCl).

Next, toluene (654.72 g) and ethyl orthoformate (2: R=Et) (271.27 g, 1.83 mol) were added dropwise to the reactor at from 75 to 85° C. After the completion of the dropwise addition, stirring was continued at from 90 to 100° C. for 13 hours. Then, the reaction mixture was cooled to a temperature of 30 to 45° C. Then, a mixture of acetic acid (176.00 g) and water (528.00 g) were added to the reactor, followed by phase separation and removal of the aqueous phase. Then, the organic phase was concentrated at a reduced pressure and foe residue was subjected to distillation at a reduced pressure to obtain a crude product, (9E)-1,1-diethoxy-9-dodecene (3-1: R=Et), (312.65 g, 1.15 mol, purity: 93.91%) in a crude yield of 81.33%.

The following are spectrum data of (9E)-1,1-diethoxy-9-dodecene (3-1: R=Et) thus produced.

[Nuclear magnetic resonance spectrum] $^1$H-NMR (500 MHz CDCl$_3$): δ0.95 (3H, t, J=73 Hz), 1.19 (6H, t, J=7.1 Hz), 1.24-1.36 (10H, m), 1.59 (2H, dt), J=9.2 Hz, 62 Hz), 1.97 (4H, sext-like, J=7.6 Hz), 3.48 (2H, dq, J=73 Hz, 8.4 Hz), 3.62 (2H, dq, J=7.3 Hz, 8.4 Hz), 4.47 (1H, t, J=5.8 Hz), 5.37 (1H, dt, J=15.7 Hz, 6.1 Hz), 5.42 (1H, dt, J=15.7 Hz, 6.1 Hz); $^{13}$C-NMR (125 MHz, CDCl$_3$): δ 13.97, 1533, 24.73, 25.57, 29.05, 29.40, 29.42, 29.59, 32.51, 33.56, 60.76, 102.93, 129.0, 131.85

[Mass spectrum] EI-Mass spectrum (70 eV): m/z 211 (M$^+$−45), 103, 75, 47, 29

[Mated absorption spectrum] (NaCl): ν=2974, 2926, 2874, 2854, 1461, 1443, 1373, 1344, 1128, 1063, 966

Example 5

Preparation of (9Z)-9-dodecenal (4-2)

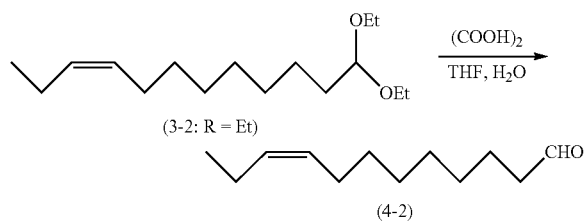

The crude product containing (9Z)-1,1-diethoxy-9-dodecene (3-2: R=Et) (641.06 g, 234 mol, purity: 93.65%) obtained in Example 3, oxalic acid dihydrate (59036 g, 4.68 mol), tetrahydrofuran (1638.70 g) and pure water (1638.70 g) were placed in a reactor at room temperature and stirred at from 60 to 65° C. for 6 hours. Subsequently, the reaction mixture was cooled to 50° C. Then, hexane (688.49 g) was added to the reactor and the reaction mixture was stirred for 30 minutes, followed by phase separation and removal of foe aqueous phase. Then, the organic phase was concentrated at a reduced pressure and the residue was subjected to distillation at a reduced pressure to obtain (9Z)-9-dodecenal (4-2) (410.32 g, 2.21 mol, purity: 98.10%) in an overall yield of 76.15% in the two steps of Examples 3 and 5.

The following are spectrum date of (9Z)-9-dodecenal (4-2) thus produced.

[Nuclear magnetic resonance spectrum] $^1$H-NMR (500 MHz CDCl$_3$): δ0.94 (3H, t, J=7.6 Hz), 1.25-1.36 (8H, m), 1.61 (2H, quin-like, J=7.3 Hz), 2.01 (4H, sext-like, J=7.3 Hz), 2.40 (2H, dt, J=1.9 Hz, 7.5 Hz), 5.26-5.38 (2H, m), 9.75 (1H, t, J=1.9 Hz); $^{13}$C-NMR (125 MHz, CDCl$_3$): δ 14.33, 20.46, 22.01, 26.97, 28.97, 29.08, 29.19, 29.60, 43.85, 129.10, 131.58, 202.86

[Mass spectrum] EI-Mass spectrum (70 eV): m/z 182 (M$^+$), 164, 135, 121, 111, 98, 81, 67, 55, 41, 29

[Mated absorption spectrum] (NaCl): ν=2962, 2929, 2855, 1727, 1463, 724

Example 6

Preparation of (9E)-9-dodecenal (4-1)

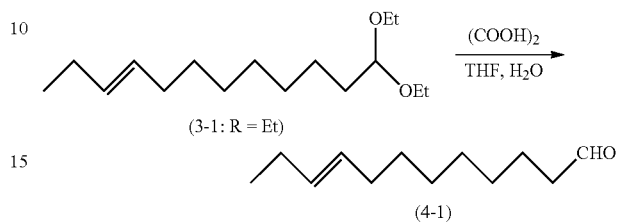

The crude product containing (9E)-1,1-diethoxy-9-dodecene (3-1: R=Et) (312.66 g, 1.15 mol, purity: 93.91%) obtained in Example 4, oxalic acid dehydrate (462.55 g, 3.67 mol), tetrahydrofuran (1223.00 g) and pure water (1223.00 g) were placed in a reactor at room temperature and stirred at from 60 to 65° C. for 5.5 hours. Subsequently, the reaction mixture was cooled to 50° C. Then, hexane (359.68 g) was added to the reactor and the reaction mixture was stirred for 30 minutes, Mowed by phase separation and removal of the aqueous phase. Then, the organic phase was concentrated at a reduced pressure and the residue was subjected to distillation at a reduced pressure to obtain (9E)-9-dodecenal (4-1) (198.10 g, 1.07 mol, purity: 98.65%) in an overall yield of 76.15% in the two steps of Examples 4 and 6.

The following am spectrum data of (9E)-9-dodecenal (4-1) thus produced.

[Nuclear magnetic resonance spectrum] $^1$H-NMR (500 MHz CDCl$_3$): δ 0.95 (3H, t, J=7.5 Hz), 1.23-1.36 (8H, m), 1.61 (2H, quin-like, J=7.3 Hz), 1.97 (4H), sext-like, J=7.7 Hz), 2.40 (2H, dt, J=1.9 Hz, 7.4 Hz), 536 (1H, dt, J=153 Hz, 6.1 Hz), 5.42 (1H, dt, J=15.3 Hz, 5.8 Hz), 9.75 (1H, t, J=1.9 Hz); $^{13}$C-NMR (125 MHz, CDCl$_3$): δ 13.94, 22.01, 25.55, 28.86, 29.07, 29.17, 29.48, 32.45, 43.86, 129.15, 131.94, 202.86

[Mass spectrum] EI-Mass spectrum (70 eV): m/z 182 (M$^+$), 164, 135, 121, 111, 98, 82, 69, 55, 41, 29

[Inferred absorption spectrum] (NaCl): ν=2961, 2927, 2854, 1727, 1462, 967

The invention claimed is:

1. A process for preparing a (9Z)- or (9E)-9-dodecenal compound of the following formula (4):

$$CH_3CH_2CH=CH(CH_2)_7CHO \quad (4)$$

the process comprising steps of
subjecting a nucleophilic reagent, a (3Z)- or (3E)-3-hexenyl compound, of the following general formula (5):

$$CH_3CH_2CH=CH(CH_2)_2M^2 \quad (5)$$

in which $M^2$ represents Li or MgZ$^2$, wherein Z$^2$ represents a halogen atom or a 3-hexenyl group, to a coupling reaction with a 1-halo-5-halopentane compound of the general formula (6):

$$X^3(CH_2)_5X^4 \quad (6)$$

in which $X^3$ represents a chlorine atom and $X^4$ represents a bromine atom, in the presence of a cuprous halide and a trialkyl phosphite compound having 3 to 9 carbon atoms to produce a (3Z)- or (3E)-11-halo-3-undecene compound of the following general formula (7):

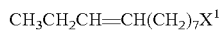  (7)

in which $X^1$ represents a chlorine atom; and
preparing the nucleophilic reagent, (8Z)- or (8E)-8-undecenyl compound of the following general formula (1);

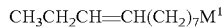  (1)

in which $M^1$ represents Li or $MgZ^1$, wherein $Z^1$ represents a halogen atom or an 8-undecenyl group,
from the (3Z)- or (3E)-11-chloro-3-undecene compound (7) thus obtained, respectively;
subjecting the nucleophilic reagent, (8Z)- or (8E)-8-undecenyl compound (1) thus obtained to a nucleophilic substitution reaction with an orthoformic ester compound of the following general formula (2):

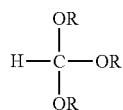  (2)

in which R may be same with or different from each other and represents an alkyl group having 1 to 6 carbon atoms, to produce a (9Z)- or (9E)-1,1-dialkoxy-9-dodecene compound of the following general formula (3):

  (3)

in which R is as defined above, respectively; and
hydrolyzing the (9Z)- or (9E)-1,1-dialkoxy-9-dodecene compound (3) thus obtained, in the presence of oxalic acid to produce the (9Z)- or (9E)-9-dodecenal compound (4), respectively.

2. The process according to claim 1, wherein the nucleophilic reagent (1) is (8E)-8-undecenyl compound, of the following general formula (1-1):

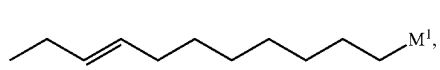  (1-1)

wherein the nucleophilic reagent (5) is (3E)-3-hexenyl compound, of the following general formula (5-1):

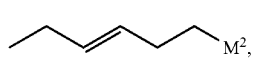  (5-1)

and
wherein the 11-halo-3-undecene compound (7) is (3E)-11-halo-3-undecene compound of the following general formula (7-1):

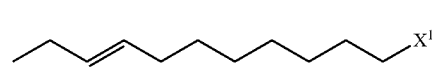  (7-1)

wherein the 9-dodecenal compound of the following formula (4) is (9E)-9-dodecenal of the following formula (4-1):

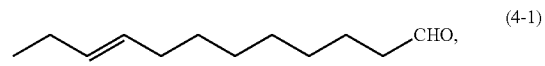  (4-1)

and
wherein the 1,1-dialkoxy-9-dodecene compound (3) is (9E)-1,1-dialkoxy-9-dodecene compound of the following general formula (3-1):

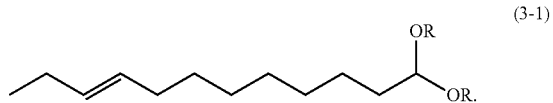  (3-1)

3. The process according to claim 1, wherein the nucleophilic reagent (1) is (8Z)-8-undecenyl compound, of the following general formula (1-2):

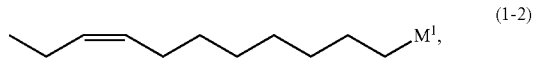  (1-2)

wherein the nucleophilic reagent (5) is (3Z)-3-hexenyl compound, of the following general formula (5-2):

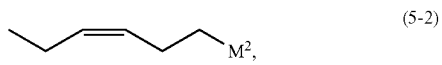  (5-2)

and
wherein the 11-halo-3-undecene compound (7) is (3Z)-11-halo-3-undecene compound of the following general formula (7-2):

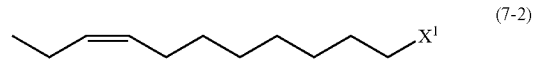  (7-2)

wherein the 9-dodecenal compound of the following formula (4) is (9Z)-9-dodecenal of the following formula (4-2):

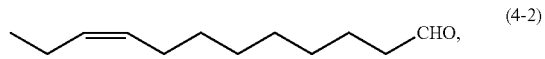  (4-2)

and
wherein the 1,1-dialkoxy-9-dodecene compound (3) is (9Z)-1,1-dialkoxy-9-dodecene compound of the following general formula (3-2):

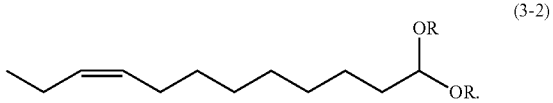  (3-2)

4. A process for preparing a 9-dodecenal compound of the following formula (4):

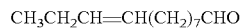  (4):

the process comprising steps of preparing a nucleophilic reagent, 8-undecenyl compound, of the following general formula (1)

$$CH_3CH_2CH=CH(CH_2)_7M^1 \qquad (1)$$

in which $M^1$ represents Li or $MgZ^1$, wherein $Z^1$ represents a halogen atom or an 8-undecenyl group from an 11-halo-3-undecene compound of the following general formula (7):

$$CH_3CH_2CH=CH(CH_2)_7X^1 \qquad (7)$$

in which $X^1$ represents a halogen atom;

subjecting, the nucleophilic reagent, 8-undecenyl compound (1) thus obtained, to a nucleophilic substitution reaction with an orthoformic ester compound of the following general formula (2):

$$\underset{\underset{OR}{|}}{\overset{\overset{OR}{|}}{H-C-OR}} \qquad (2)$$

in which R may be same with or different from each other and represents an alkyl group having 1 to 6 carbon atoms, to produce a 1,1-dialkoxy-9-dodecene compound of the following general formula (3):

$$CH_3CH_2CH=CH(CH_2)_7CH(OR)_2 \qquad (3)$$

in which R is as defined above; and hydrolyzing the 1,1-dialkoxy-9-dodecene compound (3) thus obtained, in the presence of oxalic acid to produce the 9-dodecenal compound (4).

* * * * *

UNITED STATES PATENT AND TRADEMARK OFFICE
CERTIFICATE OF CORRECTION

PATENT NO. : 12,116,328 B2
APPLICATION NO. : 16/922679
DATED : October 15, 2024
INVENTOR(S) : Miyake et al.

It is certified that error appears in the above-identified patent and that said Letters Patent is hereby corrected as shown below:

In the Specification

Column 1, Line 56: Please correct "Nat-Patent" to read --Non-Patent--

Column 1, Line 62: Please correct "repotted" to read --reported--

Column 3, Line 1: Please correct "in which may" to read --in which R may--

Column 4, Line 25: Please correct "foe" to read --the--

Column 5, Line 54: Please correct "tetrahydrofiuan," to read --tetrahydrofuran,--

Column 6, Line 1: Please correct "foe" to read --the--

Column 7, Line 56: Please correct "colliding" to read --coupling--

Column 7, Line 62: Please correct "foe" to read --the--

Column 7, Line 65: Please correct "hum" to read --from--

Column 8, Line 1: Please correct "foe" to read --the--

Column 8, Line 7: Please correct "hum" to read --from--

Column 9, Line 13: Please correct "foe" to read --the--

Column 9, Line 32: Please correct "(8K)-8-undecenyl compound (1-1)," to read --(8E)-8-undecenyl compound (1-1),--

Column 10, Line 6: Please correct "hum" to read --from--

Signed and Sealed this
Eighth Day of July, 2025

Coke Morgan Stewart
*Acting Director of the United States Patent and Trademark Office*

Column 10, Line 35: Please correct "fee" to read --the--

Column 11, Line 8: Please correct "ortho formic" to read --orthoformic--

Column 11, Lines 65-66: Please correct "(97)-1,1-dialkoxy-9-dodecene" to read --(9Z)-1,1-dialkoxy-9-dodecene--

Column 12, Line 44: Please correct "earned" to read --carried--

Column 12, Line 46: Please correct "add" to read --acid--

Column 12, Line 50: Please correct "add" to read --acid--

Column 14, Line 16: Please correct "md)," to read --mol),--

Column 15, Line 8: Please correct "(6: $X^3$ = Br; $X^4$ = Q) (37123 g," to read --(6: $X^3$ = Br, $X^4$ = Cl) (371.23 g,--

Column 15, Line 25: Please correct "1.27-138" to read --1.27-1.38--

Column 15, Line 29: Please correct "25.38," to read --25.58.--

Column 16, Line 22: Please correct "J=72 Hz)," to read --J=7.2 Hz),--

Column 16, Lines 22-23: Please correct "82 Hz)," to read --8.2 Hz),--

Column 16, Line 23: Please correct "82 Hz)," to read --8.2 Hz),--

Column 17, Line 14: Please correct "J=73" to read --J=7.3--

Column 17, Line 15: Please correct "62 Hz)," to read --6.2 Hz),--

Column 17, Line 16: Please correct "J=73" to read --J=7.3--

Column 17, Line 19: Please correct "1533," to read --15.33,--

Column 17, Line 24: Please correct "[Mated" to read --[Infrared--

Column 17, Line 45: Please correct "(59036 g," to read --(590.26 g,--

Column 17, Line 57: Please correct "date" to read --data--

Column 18, Line 1: Please correct "[Mated" to read --[Infrared--

Column 18, Line 33: Please correct "am" to read --are--

Column 18, Line 38: Please correct "536" to read --5.36--

Column 18, Line 38: Please correct "J=153 Hz," to read --J=15.3 Hz,--

Column 18, Line 46: Please correct "[Inferred" to read --[Infrared--